(12) United States Patent
Gawthrop

(10) Patent No.: US 7,626,102 B2
(45) Date of Patent: Dec. 1, 2009

(54) **METHOD OF PRODUCING HYBRID *ERYSIMUM CHEIRI* SEEDS AND PLANTS USING MALE STERILITY**

(75) Inventor: Frances Gawthrop, Ash (GB)

(73) Assignee: A. L. Tozer Ltd, Cobham, Surrey (GB)

( * ) Notice: Subject to any disclaimer, the term of this patent is extended or adjusted under 35 U.S.C. 154(b) by 0 days.

(21) Appl. No.: 10/384,068

(22) Filed: Mar. 7, 2003

(65) Prior Publication Data

US 2003/0233687 A1 Dec. 18, 2003

(30) Foreign Application Priority Data

Jun. 14, 2002 (GB) ................... 0213749.5

(51) Int. Cl.
*A01H 5/00* (2006.01)
*A01H 1/02* (2006.01)
(52) U.S. Cl. ...................... 800/323; 800/274
(58) Field of Classification Search ............... 800/323, 800/303, 274
See application file for complete search history.

(56) References Cited

U.S. PATENT DOCUMENTS 3,861,079 A     1/1975   Patterson
PP13,432 P2 *  12/2002   Tristram

FOREIGN PATENT DOCUMENTS

EP    0 513 884 A    11/1992
WO    WO 94 25593 A  11/1994
WO    WO 02 16622 A   2/2002

OTHER PUBLICATIONS

Pierik, R. In Vitro Culture of Higher Plants, 1997. Kluwer Academic Publishers, pp. 183-185.*
The New Royal Horticulture Society Dictionary of Gardening. 1992, vol. 2, D to K, The MacMillan Press Limited, pp. 206-207.*
Budar, F., et al., 2001. Male sterility in plants: occurrence, determinism, significance and use. Compt. Rend. Sci. Serie III: Sci. de la Vie. Elsevier. 324(6):543-550.
Williams, M.E., 1995. Genetic engineering for pollination control. Trends Biotech. 13(9):344-349.

* cited by examiner

*Primary Examiner*—June Hwu
(74) *Attorney, Agent, or Firm*—Jondle & Associates, P.C.

(57) ABSTRACT

A method is disclosed for creating and utilizing genetic male-sterile *Erysimum cheiri* plants for hybrid wallflower production. The method makes use of a mutated male sterility allele, which suppresses pollen production in otherwise fertile plants. Individual plants expressing the male sterility factor are incapable of self-pollination and can be used as female parents in hybrid seed production. Methods are disclosed for transferring this system into any line of interest for use in hybrid seed production in *Erysimum cheiri*.

16 Claims, No Drawings

METHOD OF PRODUCING HYBRID *ERYSIMUM CHEIRI* SEEDS AND PLANTS USING MALE STERILITY

BACKGROUND OF THE INVENTION

The present invention relates to an *Erysimum cheiri* (also called wallflower) seed, an *Erysimum cheiri* plant, *Erysimum cheiri* varieties and *Erysimum cheiri* hybrids, which contain one or more male sterility alleles. This invention further relates to a method for producing *Erysimum cheiri* ($F_1$) hybrid seed and plants.

The wallflower is a popular spring and early summer bedding plant in the United Kingdom and Northern Europe and a number of different varieties are widely available. It originates from a wild flower, growing on walls, cliffs and rocks in Greece and the Aegean. English wallflower grows best in full sun or light shade and in a well-drained soil. The plants exhibit a full range of flower colors including white, yellow, red, orange, purple and intermediates. The plant is a biennial in cold climates, in warm climates it is a short-lived perennial. Most varieties are 12 to 30 inches tall and usually have fragrant flowers. Some winter protection is needed in colder climates.

Field crops including ornamentals, are bred and produced through methods that take advantage of the plant's method of pollination. Cross-pollinated crops, including all existing commercial varieties of *Erysimum cheiri*, rely on the ability of a flower to transfer functional pollen from its anthers to its stigma, thus resulting in formation of seeds. A true breeding line can be produced by successive self-pollination of a selected plant. Repeated selfing or inbreeding, however, results in genetic weakness, variously described as inbreeding depression. Vigor can be restored to true breeding lines by intercrossing in isolation, resulting in uniform progenies that can be marketed as uniform open pollinated cultivars.

Alternatives to the open-pollinated *Erysimum cheiri* varieties are $F_1$ hybrids. In $F_1$ hybrid varieties, pollen from an inbred "male" line is used to pollinate an inbred, but genetically different "female" line. The resulting $F_1$ hybrids are both phenotypically uniform and vigorous. In addition to this hybrid vigor, hybrids also offer opportunities for the rapid and controlled deployment of dominant genes for resistance to diseases and pests. A homozygous dominant gene in one parent of a hybrid will result in all $F_1$ hybrids expressing the dominant gene phenotype.

Much progress has been made in the improvement of horticultural and agronomic crops over the past several decades. Prominent among the methods used has been that of $F_1$ hybrid seed production. Essentially all corn, tomato, cucumber, and vegetable crops in general, are grown from $F_1$ hybrid seed. Ornamentals including petunias, geraniums, impatiens, snapdragons, and many others are grown as $F_1$ hybrids. Within the seed trade industry, $F_1$ hybrids command the preeminent role because of their superior vigor, uniformity and performance.

Male sterility, both naturally occurring and artificially induced, is a means of achieving controlled hybridization by the prevention of self-pollination in plants, aside from manual emasculation. In male sterility (ms) systems, absence of pollen in normally hermaphroditic flowers precludes the possibility that flowers will pollinate themselves. Without access to pollen, sexual fusion of the male and female gametes that would normally lead to seed development does not occur; the end consequence is that no "self" seed (i.e. seed arising from self-pollinations) is produced.

In higher plants, two major types of male sterility can be distinguished according to their genetic control. Genetic male sterility (GMS), sometimes referred to as genic, nuclear, or Mendelian sterility is controlled by genes carried and expressed within the nucleus of cells. Inheritance of genetic male sterility typically follows normal Mendelian segregation patterns. In contrast, cytoplasmic male sterility (CMS) is governed by cytoplasmic factors, principally the mitochondrial genome; inheritance of cytoplasmic male sterility does not follow Mendelian patterns and instead, is associated with maternal transmission of mitochondrial components from generation to generation. Neither GMS or CMS is known to occur in any *Erysimum* species, but GMS is known to occur naturally elsewhere in the Cruciferae family (Tsunoda S, Hinata K, and Gomez-Campo C (1980) Brassica Crops and Wild Allies. Japan Scientific Societies Press).

Open-pollination is an important and universal component of the reproductive biology of wallflower species. For effective commercial production of $F_1$ hybrid *Erysimum cheiri* cultivars the use of male sterility genes would be valuable.

SUMMARY OF THE INVENTION

The present invention relates to an *Erysimum cheiri* seed, an *Erysimum cheiri* plant, *Erysimum cheiri* varieties, *Erysimum cheiri* hybrids and a method for producing hybrid *Erysimum cheiri* seed. More specifically, the invention relates to an *Erysimum cheiri* plant having the male sterility alleles of the present invention. The present invention further relates to a method of producing hybrid *Erysimum cheiri* seeds using a male sterility system. The present invention further relates to a method of producing $F_1$ hybrid *Erysimum cheiri* seed wherein said *Erysimum cheiri* seed comprises less than 2.0% self-pollinated seed. The present invention also relates to a method of producing hybrid *Erysimum cheiri* seeds and plants by crossing a male sterile plant of the instant invention with another *Erysimum* plant. The present invention further relates to a method of producing seed by growing male sterile, vegetatively produced (either as cuttings or through tissue culture) *Erysimum* plants with male fertile pollinator plants. The invention also relates to the transfer of the genetic male sterility alleles into other genetic backgrounds.

DETAILED DESCRIPTION OF THE INVENTION

In order to provide an understanding of several of the terms used in the specification and claims, the following definitions are provided.

Allele—A form in which a gene may occur. Different alleles of a gene give rise to different expressions of a character.

Hybrid—As used herein, the term "hybrid" is intended to refer to first generation $F_1$ seed or resulting progeny from crossing two non-identical parental lines. Parental lines may be related, as in production of a modified single cross, or unrelated.

Hybrid Variety—As used herein, the term "hybrid variety" is a variety produced by the cross-pollination of two parental lines. $F_1$ hybrid seed may be collected from one or both parents depending on the system employed.

Inbred Line—As used herein, an "inbred line" is a group or set of related plants reproduced by inbreeding which are phenotypically and genotypically similar.

Open-Pollinated Seed—As used herein, an "open-pollinated seed" means the seed arising from fusion of male and female gametes produced by multiple male genotypes.

Self-Pollinated Seed—As used herein, a "self-pollinated seed" means the seed arising from the fusion of male and female gametes of the same plant. In hybrid seed production, selfed or sib seed refers to that portion of the seed within a single capsule that was fathered by pollen from the female genotype rather than pollen from the intended "male" parent.

Micropropagation—the development and multiplication of plants in vitro.

Vegetative Propagation—the multiplication of plants through cuttings.

Genetic studies were conducted with the new male-sterile, female fertile *Erysimum cheiri* mutant of the present invention. This mutant was completely male-sterile and was inherited as two recessive alleles designated "$msTS_1$" and "$msTS_2$".

To date, there are no known male sterility alleles in *Erysimum cheiri* other than the present invention. The mutant alleles of the present invention allow seed set on the female plants. The genetic data indicate the male-sterile *Erysimum cheiri* ("ms") of the present invention is genetic male-sterility and is controlled by at least two recessive alleles.

The male sterility system of the present invention enables the commercial production of hybrid *Erysimum cheiri* seed. Integral to the method is reduction of self-pollination to less than 2% in the designated female parent. Prevention of selfing in the female was accomplished by the introduction of the male sterility alleles of the present invention into the intended female line. Segregation of the male sterility alleles in subsequent generations was monitored by presence/absence of normal anthers and of functional pollen. Progeny derived from self-pollinated hybrid plants were scored for presence of the male sterility segregates as well as ornamentally valuable horticultural traits. Eventually, suitable female plants were identified that were male sterile as well as horticulturally suitable.

Male, or "pollen," lines do not carry both the male sterility alleles. These lines are specifically selected to produce copious amounts of viable pollen, as assessed by methods known to those skilled in the art. Male lines are also selected for desirable horticultural traits including, but not limited to, flower color, plant height, uniformity and plant habit. Pollen from the male is collected and transferred using common methods known to those in the art.

$F_1$ hybrid seed is produced by pollination of the female line (having and expressing homozygous $msTS_1$ and $msTS_2$) with pollen from the male line. The $F_1$ seed is germinated and grown to maturity using standard methods common to the nursery trade. The resulting $F_1$ generation is assessed for phenotypic uniformity, vigor and horticultural suitability. By monitoring inheritance of known recessive genetic traits carried in the female, (especially male sterility and flower color) and their disappearance in the $F_1$ generation due to expression of dominant alleles from the male parent, the lack of selfing in the female was confirmed. Segregation of male sterility in subsequent generations further clarifies the genetic nature of the male sterility system. After horticulturally appropriate female x male combinations are found, the corresponding male and female lines can be mass propagated and used for commercial $F_1$ seed production. *Erysimum cheiri* is readily propagated by vegetative cuttings and tissue culture, although seed propagation of male parents is possible, using common methods routinely employed in line maintenance for hybrid seed production by those knowledgeable in the art.

Deployment of the male sterile alleles of the present invention in *Erysimum cheiri* enables commercial $F_1$ hybrid seed production without manual emasculation. By using the method of the present invention, $F_1$ hybrid *Erysimum cheiri* not only possesses profound vigor advantages but also provides opportunity for commercial production of unique colors, habits and other horticulturally interesting traits achievable only in the heterozygous state.

By pollinating a homozygous female with a homozygous but genetically different male, the resultant progeny will be heterozygous for many gene loci. In the breeding development of the parents, genetic backgrounds of the male and female are kept separate and intentionally selected for genetic divergence. When finally united in the $F_1$ generation, heterozygosity for a large number of gene loci imparts broad-based hybrid vigor with controlled deployment of dominant alleles expressed in the hybrid.

EXAMPLES

The following examples are provided to further illustrate the present invention and are not intended to limit the invention beyond the limitations set forth in the appended claims and amendments.

Example 1

Overview of the Method of Developing $F_1$ Hybrids

Production of $F_1$ hybrid seed in *Erysimum cheiri* utilizes male sterility expressed in the female or "seed" parent. By possessing male sterile alleles of the present invention, the female is unable to self-pollinate; as such, self-set seed is not produced. In the breeding development of the female, horticulturally desirable traits are accumulated in the female line using methods known to those in the art. The female line is repetitively inbred or sib-crossed leading to the production of male sterile females that lack functional pollen and that are potentially suitable for use in commercial hybrid seed production.

The male or pollen parent is similarly bred for desirable horticultural qualities using methods known to those in the art. Unlike the female, pollen quality and quantity are important selection components in the developmental breeding process of the male.

When appropriate male and female lines have been developed, pollinations are performed wherein pollen is removed from the male plant using methods known to those skilled in the art, and transferred to female receptive stigmas. Subsequent to these pollinations, normal seed development processes occur in the female plant ultimately resulting in seed formation. Numerous experimental male and female combinations are tried, resulting in many experimental $F_1$ hybrid progenies. Each progeny is then evaluated for presence of characters deemed horticulturally desirable. Genetic markers (such as color difference) can be used to ascertain complete absence of self-set seed from the female. Eventual evaluation of various male/female combinations can lead to appropriate combinations which can then be used in commercial $F_1$ hybrid seed production.

Example 2

Development of the ms Alleles

Male sterility has not been reported in any *Erysimum* germplasm. The mutation for male sterility was discovered in the *Erysimum cheiri* breeding material at A. L. Tozer Ltd. and was derived from the self-pollination of cultivated varieties. Crosses between the discovered male sterile plant, designated TZ9381, and breeding lines were made to establish its reality and inheritance and it was found to be transferable through successive generations. The male sterility is previously unknown and is not currently used in any horticultural wallflower varieties.

The flowers of the sterile plants are similar in size to the majority of wallflower varieties. The sepals, petals and style appear normal but the anthers are either absent or non-functional, being very reduced in size. The male sterility is controlled by two recessive genes.

The seed supplied contains the male sterility genes and male sterile plants can be identified in the F2 generation.

Example 3

A Genetic Basis for Male Sterility in *Erysimum cheiri*

The discovered plant, designated TZ9381, has white flowers and was used as a female in crosses with various, fertile *Erysimum cheiri* inbred breeding lines (Table 1). Pollinated flowers in these crosses produced fruits and seeds, demonstrating female fertility in plant TZ9381. These seeds were germinated and grown using standard methods known to those in the nursery industry. Resultant progenies were scored for presence/absence of viable pollen as well as inheritance of horticultural characters (e.g., flower color, habit). Where a male parent with colored flowers was used to pollinate the white flowered, female parent; resultant seed produced progeny with colored flowers clearly demonstrating that progeny were true hybrids and not apomictic.

As shown in Table 1, all $F_1$ hybrid progeny are pollen fertile, an observation consistent with diallelic recessive allele control, such as reported in corn (Patterson, U.S. Pat. No. 3,861,079) and *Brassica napus* L (Heyn F W (1973) Dissert. Georg August Univ. Gottingen pp 1-102 as reported by Tsunoda S, Hinata K, and Gomez-Campo C (1980) Brassica Crops and Wild Allies. Japan Scientific Societies Press). Selfing of $F_1$ progenies (See Table 1) further indicates that male sterility in the initial male sterile plant (TZ9381) was controlled by two recessive alleles, designated herein as $msTS_1$ and $msTS_2$. Segregation in the $F_2$ accords with the expected 1:15 ratio of male sterile: fertile $\chi^2=10.68$ with 16 degrees of freedom p=0.75-0.90. As shown in Table 2, test crosses between the male sterile plant and fertile $F_1$ hybrids suggest that the male sterile phenotype was controlled by two recessive alleles. Segregation accords with the expected 1:3 ratio of male sterile: fertile $\chi^2=5.16$ with 5 degrees of freedom p=0.25-0.5.

Example 4

Deployment of *Erysimum cheiri* "$msTS_1$" and "$msTS_2$"

Subsequent to introgression of "$msTS_1$" and "$msTS_2$" alleles, crosses between the original male sterile plant and fertile $F_1$ hybrids from this breeding program are shown in Table 2. The pattern of segregation confirms that male sterility in *Erysimum cheiri* is inherited in a normal fashion consistent with recessive genetic control. Moreover, that $F_1$ seed can be produced at all indicates that female function (ovule and seed production ability) is unaffected in male sterile lines. $F_1$ seed yield is at least equivalent to open-pollinated *Erysimum cheiri* flowers, suggesting that the male sterility alleles of the present invention specifically affect male function rather than overall fertility aspects.

TABLE 2

Crosses between Male Sterile TZ9381 and Fertile $F_1$ Hybrids

| Cross | | $F_1$ Generation | | |
|---|---|---|---|---|
| Female Parent | Color | Male Parent | Number Sterile | Number Fertile |
| TZ9381 | white | H1 | 3 | 5 |
| TZ9381 | white | I1 | 2 | 16 |
| TZ9381 | white | J1 | 3 | 5 |
| TZ9381 | white | K1 | 2 | 16 |
| TZ9381 | white | L1 | 2 | 16 |
| TZ9381 | white | M1 | 2 | 7 |

Deposit Information

A deposit of *Erysimum cheiri* seeds containing the $msTS_1$ and $msTS_2$ alleles for male sterility disclosed above and recited in the appended claims has been made with the American Type Culture Collection (ATCC), 10801 University Boulevard, Manassas, Va. 20110. The date of deposit was Jan. 23, 2002. The deposit of 2,500 seeds was taken from the same deposit maintained by A. L. Tozer LTD since prior to the filing date of this application. All restrictions upon the deposit have been removed, and the deposit is intended to meet all of the requirements of 37 C.F.R. §1.801-1.809. The ATCC accession number is PTA-4003. The deposit will be maintained in the depository for a period of 30 years, or 5 years after the last

TABLE 1

Crosses between Male Sterile TZ9381 and fertile inbred breeding lines

| Cross | | | $F_1$ Generation | | | $F_2$ Generation | | |
|---|---|---|---|---|---|---|---|---|
| Female Parent | Color | Male Parent | Color | Number Sterile | Number Fertile | Color | Number Sterile | Number Fertile |
| TZ9381 | white | A1 | Pale Yellow | 0 | 20 | Pale yellow | 1 | 19 |
| TZ9381 | white | B1 | Pale Yellow | 0 | 40 | Pale Yellow | 1 | 15 |
| TZ9381 | white | C1 | Pale orange | 0 | 40 | Pale orange | 1 | 17 |
| TZ9381 | white | C2 | Pale orange | 0 | 20 | Pale orange | 1 | 17 |
| TZ9381 | white | D1 | Bright orange | 0 | 40 | Bright orange | 2 | 16 |
| TZ9381 | white | E2 | Bronze | 0 | 20 | Yellow + orange | 1 | 17 |
| TZ9381 | white | E3 | Bronze | 0 | 20 | Yellow + orange | 1 | 17 |
| TZ9381 | white | F1 | Pink | 0 | 20 | V pale orange | 1 | 17 |
| TZ9381 | white | G2 | Pink | 0 | 40 | V pale orange | 2 | 16 | request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention.

The invention claimed is:

1. A female fertile, male sterile *Erysimum cheiri* plant, or a part thereof, produced by selfing an *Erysimum cheiri* plant grown from, *Erysimum cheiri* seed designated TZ9843 deposited under ATCC Accession Number PTA-4003.

2. A female fertile, male sterile *Erysimum cheiri* seed produced by the plant of claim 1.

3. A plant grown from the seed of claim 2.

4. An ovule of the plant of claim 1.

5. The plant of claim 1 propagated by a method selected from the group consisting of vegetative cuttings and embryo rescue.

6. A tissue culture comprising regenerable cells of the plant of claim 1.

7. An *Erysimum cheiri* plant regenerated from said tissue culture that is female fertile and male sterile of claim 6.

8. A method for producing a hybrid *Erysimum cheiri* seed, comprising crossing a first parent *Erysimum cheiri* plant with a second parent *Erysimum cheiri* plant and harvesting the resultant hybrid *Erysimum cheiri* seed, wherein said first parent *Erysimum cheiri* plant is the *Erysimum cheiri* plant of claim 1.

9. A hybrid seed that is female fertile and male sterile produced by the method of claim 8.

10. A hybrid plant or a part thereof that is female fertile and male sterile produced by growing said hybrid seed of claim 9.

11. A female fertile, male sterile *Erysimum cheiri* plant, or a part thereof, produced by crossing an *Erysimum cheiri* plant grown, *Erysimum cheiri* seed designated TZ9843 deposited under ATCC Accession Number PTA-4003 with one or more *Erysimum cheiri* plants grown from, *Erysimum cheiri* seed designated TZ9843 deposited under ATCC Accession Number PTA-4003.

12. A method of producing a female fertile, male sterile *Erysimum cheiri* plant, comprising:
    a) growing *Erysimum cheiri* seed designated TZ9843 deposited under ATCC Accession Number PTA-4003 to produce an *Erysimum cheiri* plant;
    b) self-pollinating said *Erysimum cheiri* plant to produce selfed seed; and
    c) growing said selfed seed and selecting a female fertile, male sterile *Erysimum cheiri* plant.

13. A method of producing a female fertile, male sterile *Erysimum cheiri* plant, comprising:
    a) growing *Erysimum cheiri* seed from progeny of *Erysimum cheiri* seed designated TZ9843 deposited under ATCC Accession Number PTA-4003 to produce an *Erysimum cheiri* plant;
    b) self-pollinating said *Erysimum cheiri* plant to produce selfed seed; and
    c) growing said selfed seed and selecting a female fertile, male sterile *Erysimum cheiri* plant.

14. A method of producing a female fertile, male sterile *Erysimum cheiri* plant, comprising:
    a) growing *Erysimum cheiri* seed designated TZ9843 deposited under ATCC Accession Number PTA-4003 to produce at least two *Erysimum cheiri* plants;
    b) crossing said *Erysimum cheiri* plants to produce seed;
    c) growing said seed of step b) to produce *Erysimum cheiri* plants; and
    d) selecting a female fertile, male sterile *Erysimum cheiri* plant from the plants of step c).

15. A method of producing a female fertile, male sterile *Erysimum cheiri* plant, comprising:
    a) growing *Erysimum cheiri* seed from progeny of *Erysimum cheiri* seed designated TZ9843 deposited under ATCC Accession Number PTA-4003 to produce at least two *Erysimum cheiri* plants;
    b) crossing said *Erysimum cheiri* plants to produce progeny seed;
    c) growing said progeny seed of step b) to produce *Erysimum cheiri* plants; and
    d) selecting a female fertile, male sterile *Erysimum cheiri* plant from the plants of step c).

16. A method of producing a female fertile, male sterile *Erysimum cheiri* plant, comprising:
    a) growing *Erysimum cheiri* seed designated TZ9843 deposited under ATCC Accession Number PTA-4003 to produce an *Erysimum cheiri* plant;
    b) growing seed from progeny of *Erysimum cheiri* seed designated TZ9843 deposited under ATCC Accession Number PTA-4003 to produce an *Erysimum cheiri* plant;
    c) crossing the *Erysimum cheiri* plant of step a with the *Erysimum cheiri* plant of step b) to produce progeny seed;
    d) growing said progeny seed of step c) to produce *Erysimum cheiri* plants; and
    e) selecting a female fertile, male sterile *Erysimum cheiri* plant from the plants of step d).

* * * * *